(12) United States Patent
Las Navas Garcia

(10) Patent No.: US 9,377,419 B2
(45) Date of Patent: Jun. 28, 2016

(54) METHOD AND APPARATUS FOR MULTIPLE SAMPLE PREPARATION AND SIMULTANEOUS LOSS OF IGNITION/GAIN ON IGNITION ANALYSIS, FOR USE IN X-RAY FLUORESCENCE SPECTROMETRY

(71) Applicant: Jose Maria Las Navas Garcia, Conway, SC (US)

(72) Inventor: Jose Maria Las Navas Garcia, Conway, SC (US)

(*) Notice: Subject to any disclaimer, the term of this patent is extended or adjusted under 35 U.S.C. 154(b) by 722 days.

(21) Appl. No.: 13/711,915

(22) Filed: Dec. 12, 2012

(65) Prior Publication Data

US 2014/0161150 A1 Jun. 12, 2014

(51) Int. Cl.

| | |
|---|---|
| *G01N 25/00* | (2006.01) |
| *G01N 23/22* | (2006.01) |
| *B01L 3/00* | (2006.01) |
| *G01N 1/44* | (2006.01) |
| *G01N 5/04* | (2006.01) |
| *G01N 5/00* | (2006.01) |
| *B01L 3/04* | (2006.01) |
| *G01N 35/04* | (2006.01) |

(52) U.S. Cl.
CPC .............. *G01N 23/2202* (2013.01); *B01L 3/00* (2013.01); *G01N 1/44* (2013.01); *G01N 5/00* (2013.01); *G01N 5/045* (2013.01); *G01N 25/00* (2013.01); *B01L 3/04* (2013.01); *G01N 2035/0439* (2013.01)

(58) Field of Classification Search
CPC ......... G01N 5/045; G01N 25/00; G01N 5/00; G01N 2035/00346; G01N 2203/0222; G01N 25/54; G01N 25/56; G01N 27/123; G01N 27/16; G01N 35/025
See application file for complete search history.

(56) References Cited

U.S. PATENT DOCUMENTS

| | | | | |
|---|---|---|---|---|
| 3,344,654 A | * | 10/1967 | Ferenc ..................... | G01G 7/02 374/14 |
| 4,329,136 A | | 5/1982 | Willay et al. | |
| 4,537,572 A | * | 8/1985 | Hill .......................... | G01N 5/00 374/14 |
| 4,681,996 A | * | 7/1987 | Collins .................... | H05B 6/80 219/679 |
| 4,770,542 A | * | 9/1988 | Takagi .................... | B29C 71/04 374/57 |
| 4,871,309 A | | 10/1989 | Chapman | |
| 5,055,264 A | * | 10/1991 | Czarnecki ............... | G01N 5/04 177/212 |
| 5,115,457 A | | 5/1992 | Lewandowski et al. | |
| 5,230,253 A | * | 7/1993 | Blough, Jr. ............ | B01F 5/0057 137/597 |
| 5,269,827 A | | 12/1993 | Lenke et al. | |

(Continued)

FOREIGN PATENT DOCUMENTS

| | | | |
|---|---|---|---|
| JP | 2000146796 A | * | 5/2000 |
| RU | 20968 U1 | | 10/2001 |
| TW | 201245720 A | | 11/2012 |

*Primary Examiner* — Gail Kaplan Verbitsky

(74) *Attorney, Agent, or Firm* — Ernest B. Lipscomb; Barnwell Whaley Patterson & Helms

(57) ABSTRACT

The analyzer mixes the material to be analyzed and the flux in sample holders supported by a movable platform within the furnace. A tilt member is provided having multiple stations. Each station has an upstanding pin offset from the center point of the station in a different direction. The platform is indexed relative to the tilt member such that the sample holder aligns with each station, in sequence. As the sample holder aligns with each station, the platform is moved toward the tilt member such that the pin of the aligned station abuts and tilts the sample holder in a different direction. The repeated tilting of the sample holder in different directions mixes the material and flux. The contents of the sample holder may also be agitated by rapidly moving the platform back and forth with sudden stops. The analyzer can be used with a special sample holder.

7 Claims, 7 Drawing Sheets

(56) References Cited

U.S. PATENT DOCUMENTS

| | | | | |
|---|---|---|---|---|
| 6,057,516 A * | 5/2000 | Nakamura | ............... | G01G 7/02 177/154 |
| 6,302,577 B1 * | 10/2001 | Jennings | ................ | G01G 19/52 177/145 |
| 7,172,729 B2 * | 2/2007 | Las Navas Garcia | .. | G01N 5/045 422/78 |
| 2003/0003016 A1 | 1/2003 | Las Navas Garcia | | |
| 2003/0007542 A1 * | 1/2003 | Peterman, Jr. | ......... | G01G 21/14 374/14 |
| 2004/0175295 A1 | 9/2004 | Garcia | | |
| 2010/0278210 A1 * | 11/2010 | Danley | ..................... | G01N 5/04 374/14 |
| 2012/0132472 A1 | 5/2012 | Las Navas Garcia | | |

* cited by examiner

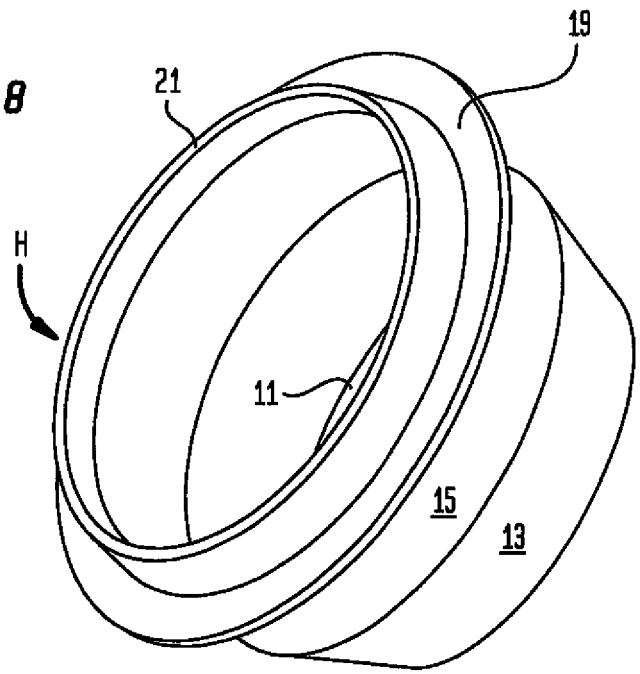
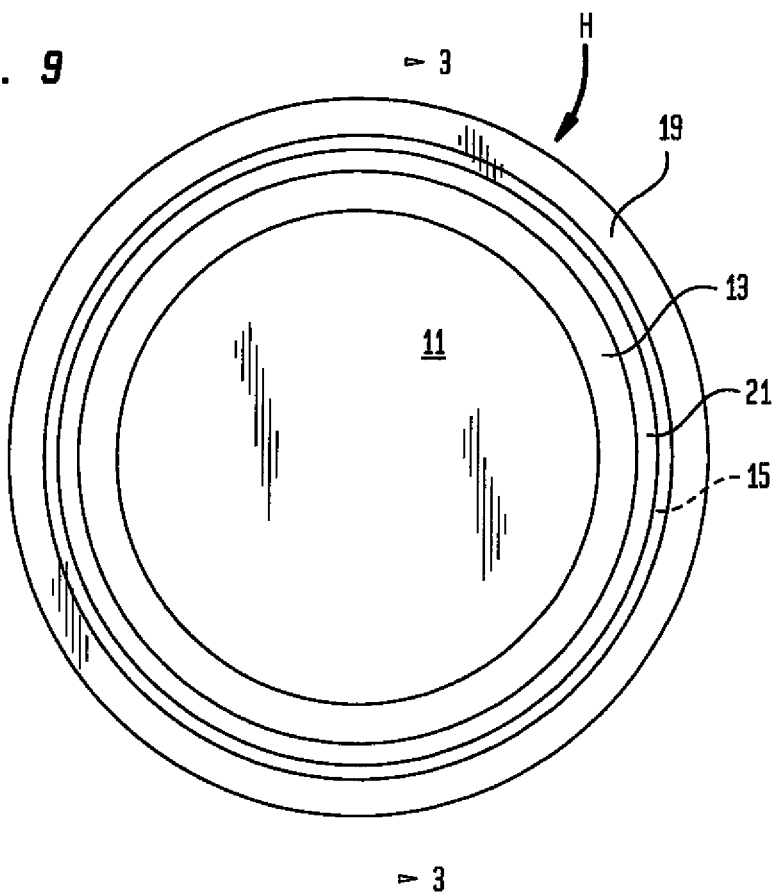

METHOD AND APPARATUS FOR MULTIPLE SAMPLE PREPARATION AND SIMULTANEOUS LOSS OF IGNITION/GAIN ON IGNITION ANALYSIS, FOR USE IN X-RAY FLUORESCENCE SPECTROMETRY

BACKGROUND OF THE INVENTION

1. Field of the Invention

The present invention relates to a method and apparatus for preparing samples for X-ray spectrometry analysis including and simultaneously loss on ignition/gain on ignition analysis, and more particularly, to a method and apparatus for preparing multiple samples for X-ray spectrometry analysis in a thermogravimetric analyzer of the type having a carousel for supporting and sequentially moving the sample holders within the furnace for weighing, in which the apparatus automatically mixes the material to be analyzed with flux to form the sample in each sample holder by repeatedly tilting the sample holders in different directions, as the carousel is moved, and in some instances, agitating the contents of the sample holders by rapidly moving the carousel back and forth with sudden stops.

2. Description of Prior Art Including Information Disclosed Under 37 CFR 1.97 and 1.98

X-ray fluorescence (XRF) is the emission of characteristic "secondary" (or fluorescent) X-rays from a material that has been excited by being bombarded with high-energy X-rays or gamma rays. The phenomenon is widely used for elemental analysis and chemical analysis, particularly in the investigation of metals, glass, ceramics and building materials, and for research in geochemistry, forensic science and archaeology.

The fusion bead method is an effective sample preparation technique for accurate XRF analysis results of ores, rocks and refractory materials since the technique eliminates heterogeneity due to grain size and mineralogical effect. The sample to be analyzed is in powder form and generally is dissolved with a lithium borate flux in a ratio 1:5, 1:10, or 1:14 at approximately 1050 C. The ratio is very important and weight precision of flux and sample within the 1-0.1 mg range is generally required.

Samples are usually never pure and loss on ignition/gain on ignition analysis is often performed with the addition of water of crystallization. Mathematical models are available for the XRF analyzer to correct deviations in the sample to flux ratio of the material as a result of sample weight changes due to volatilization.

Nevertheless, it is quite common to perform loss on ignition/gain on ignition analysis prior to XRF analysis and to introduce the results of the loss on ignition/gain on ignition analysis to the XRF spectrometer to obtain accurate results.

Preparation of fused samples (commonly referred to as "beads") is a tedious and time consuming task. It requires precision sample weighing, precision flux weighing, dangerous manipulation of very hot components, and cleaning of crucibles in citric acid.

If loss on ignition/gain on ignition analysis is required, an additional operation is needed to analyze the loss on ignition/gain on ignition valve of a different part of the same sample and provide this information to the XRF spectrometer for proper analytical results.

Thermogravimetric analyzers (TGA) are well known in the art as being used to analyze the moisture and other volatile content of ash (coal and coke) samples using loss on ignition/gain on ignition analysis. Such thermogravimetric analyzers include a furnace which heats the sample in a crucible to about 1000 degrees to evaporate the moisture and volatile constituents. The sample is weighed prior to being placed in the furnace and after it is heated to the desired temperature within the furnace. The weights are then compared to ascertain the amount of moisture and other volatile substances present in the sample.

The loss on ignition/gain on ignition analysis process has been automated by constructing the furnace with an opening on the top surface through which sample-containing crucibles can be inserted into and removed from the interior of the furnace. That allows the samples to be placed in the furnace and withdrawn from the furnace without opening the furnace door, thereby eliminating the heat loss and temperature fluctuation inherent in repeatedly opening the furnace door during the analysis.

Further, a carousel capable of retaining multiple sample-containing crucibles is provided within the furnace. The carousel supports the crucibles in the furnace while they are being heated in the furnace and then transports the crucibles, one at a time, into alignment with a scale for weighing.

An auto-loader can be provided for placing the crucibles on the internal carousel for heating and weighing, and for removing the crucibles from the internal carousel after they are weighed. An automated thermogravimetric analyzer of this type is disclosed in U.S. Pat. No. 7,172,729, issued Feb. 6, 2007 to applicant, which patent is incorporated herein by reference.

That patent discloses a robotic arm type auto-loader. However, other types of automatic loading mechanisms may be used to insert and remove the sample-containing crucibles from the furnace. For example, a more sophisticated auto-loader including a multi-crucible retaining external carousel, which is both rotatable and linearly movable toward and away from furnace opening, may be used. Such an auto-loader is provided in the Multi-matrix, multi-sample MMS-4000 TGA sold by Navas Instruments of Conway, S.C.

Thermogravimetric analyzers performing loss on ignition/gain on ignition analysis utilize ceramic crucibles with rounded interior bottom surfaces designed to cause the melted samples to accumulate at the lowest point on the bottom surface. However, such crucibles are not suitable for X-ray spectrometry analysis, as is explained below.

X-ray spectrometry analysis is also well known in the art for determining the composition of materials such as ores, cement and the like using X-ray fluorescence techniques. In order to perform X-ray spectrometry analysis, the sample is placed in a sample holder (crucible) suitable for X-ray spectrometry analysis and mixed with flux, such as lithium tetraborate, to form a homogeneous mixture. The crucible with the sample-flux mixture is heated and fused in a furnace to a high temperature. The homogeneous mixture is then normally poured to a casting dish for forming and cooling. The resulting material is called a fluxer.

The casting dish suitable for this process must prevent the bead from sticking to the sides of the dish after the fluxer bead has cooled. Once the bead has cooled, the casting dish with the fluxer bead is transferred to the X-ray spectrometry instrument for analysis. X-ray spectrometry requires that the casting dish have a flat bottom on which the cooled bead rests in order to provide an accurate result. Accordingly, the ceramic crucible with the rounded bottom normally used for the loss on ignition/gain on ignition analysis is not suitable for use in X-ray spectrometry analysis.

However, the loss on ignition/gain on ignition analysis and the X-ray spectrometry analysis are related because the accuracy of the X-ray spectrometry analysis is dependent upon having a sample with a known sample-to-flux ratio. Heating the sample to form the bead eliminates some of the volatile materials from the sample and therefore changes the sample-to-flux ratio of the sample.

It is therefore known to adjust the results of the X-ray spectrometry analysis to take into account the amount of volatile material in the sample. If the amount of volatile material in the sample is not known, it can be determined by first performing a loss on ignition/gain on ignition analysis on the sample in a thermogravimetric analyzer. The results of that analysis can then be provided to the computer associated with the X-ray spectrometry instrument. The computer will use the result of the loss on ignition/gain on ignition analysis to adjust for the loss of volatile materials from the sample, in order to increase accuracy of the X-ray spectrometry analysis.

Presently, when the loss on ignition/gain on ignition analysis is performed on a sample, the sample is split in two portions. One portion of the sample is used for the thermogravimetric analysis. The other portion of the sample is used for X-ray spectrometry analysis. The data from the loss on ignition/gain on ignition analysis of the first sample portion, performed in the thermogravimetric analyzer, is sent to the spectrometer for ratio correction.

The other portion of the sample is then weighed into a container and a measured amount of flux is added to the sample. The sample and flux are then agitated vigorously to obtain a homogeneous mixture and the homogeneous mixture, in the container, is placed in a furnace for fusing. After the sample is fused, the container with sample and flux is removed from the furnace the mixture is poured in the casting dish and allowed to cool to obtain the fluxer bead.

Ceramic crucibles suitable for use in the loss on ignition/gain on ignition analysis generally have a round bottoms. However, containers for use in X-ray analysis are made of metal and must have a non-stick surface and a flat bottom. Accordingly, preparation of samples for X-ray spectrometry analysis cannot be presently be performed in the thermogravimetric analyzer in which the loss on ignition/gain on ignition analysis is performed in a continuous, automated process because the crucibles used in the thermogravimetric analyzer are not suitable for use in X-ray spectrometric analysis.

That is so even if platinum crucibles were used for X-ray spectrometry. That is because the sample and flux must be thoroughly mixed obtain the homogeneous mixture necessary to form fluxed beads and the sample-flux mixing operation requires the removal of the sample-containing crucible from the furnace.

However, with the present invention, it is now possible to perform the loss on ignition/gain on ignition analysis and the X-ray spectrometry sample preparation in a single instrument, in a continuous, fully automated process. The present invention substantially reduces the amount of time, labor and expense of performing the loss on ignition/gain on ignition analysis and the X-ray spectrometry analysis sample preparation, both of which can now take place in a single instrument. In particular, the use of a unique sample holder and the use of a mechanism situated within the furnace to mix the sample and flux to obtain the homogenous mixture allows the entire process to be fully automated, such that both tasks can be performed on multiple samples in the furnace, without having to remove the samples for mixing, and thus without operator assistance.

It is, therefore, a prime object of the present invention to provide a method and apparatus for preparing a sample for X-ray spectrometry analysis in a modified thermogravimetric analyzer.

It is another object of the present invention to provide a method and apparatus for preparing a sample for X-ray spectrometry analysis in a modified thermogravimetric analyzer capable of performing loss on ignition/gain on ignition analysis.

It is another object of the present invention to provide a method and apparatus for preparing a sample for X-ray spectrometry analysis in a modified thermogravimetric analyzer in which X-ray spectrometric analysis sample preparation can be performed with or without loss on ignition/gain on ignition analysis.

It is another object of the present invention to provide a method and apparatus for preparing a sample for X-ray spectrometric analysis in a modified thermogravimetric analyzer such that the loss on ignition/gain on ignition analysis value of the sample may be taken into account in performing X-ray spectrometry to compensate for the volatile material lost during heating of the sample.

It is another object of the present invention to provide a method and apparatus for preparing a sample for X-ray spectrometric analysis in a modified thermogravimetric analyzer wherein a single sample holder can be used for the loss on ignition/gain on ignition analysis and for the X-ray spectrometry analysis.

It is another object of the present invention to provide a method and apparatus for preparing a sample for X-ray spectrometric analysis in a modified thermogravimetric analyzer using a sample holder having a shape and made of material which prevents the cooled sample from sticking to it and which has a flat bottom suitable for X-ray spectrometry analysis thus eliminating the necessity for pouring molten samples from one container to another.

It is another object of the present invention to provide a method and apparatus for preparing a sample for X-ray spectrometric analysis in a modified thermogravimetric analyzer wherein a homogeneous mixture of the material to be analyzed and the flux is created by mixing the material to be analyzed and the flux within the furnace of the thermogravimetric analyzer.

It is another object of the present invention to provide a method and apparatus for preparing a sample for X-ray spectrometric analysis in a thermogravimetric analyzer which has been modified to repeatedly tilt the sample holders retained on the internal carousel in different directions as the carousel is rotated to transport sample holders into and out of alignment with the scale of the thermogravimetric analyzer to form the homogenous mixture necessary to obtain the bead.

It is another object of the present invention to provide a method and apparatus for preparing a sample for X-ray spectrometric analysis in a thermogravimetric analyzer which has been modified to agitate the contents of the sample holders by moving the sample holders back and forth rapidly with sudden stops after the sample holders have been tilted.

It is another object of the present invention to provide a method and apparatus for preparing a sample for X-ray spectrometry analysis in a modified thermogravimetric analyzer wherein multiple samples can be subjected to loss on ignition/gain on ignition analysis and preparation for X-ray spectrometric analysis in a single, continuous process.

It is another object of the present invention to provide a method and apparatus for preparing a sample for X-ray spectrometric analysis in a modified thermogravimetric analyzer wherein multiple samples can be automatically subjected to loss on ignition/gain on ignition analysis and preparation for X-ray spectrometric analysis without operator assistance.

It is another object of the present invention to provide a modified thermogravimetric analyzer suitable for sample preparation for X-ray spectrometry analysis.

It is another object of the present invention to provide a unique sample holder which can be used for both loss on ignition/gain on ignition analysis and for sample preparation for X-ray spectrometry analysis.

BRIEF SUMMARY OF THE INVENTION

Those objects are achieved by the present invention in which one aspect relates to a thermogravimetric analyzer including a furnace, a sample holder situated within the furnace, and means for mixing the material to be analyzed and flux within the sample holder. The mixing means includes a platform within the furnace upon which the sample holder is supported. A tilt member is provided having station with a center point and an upstanding pin offset from the center point. Means are provided moving the platform relative to the tilt member such that the sample holder aligns with the tilt member station and the pin of the aligned tilt member station abuts and tilts the sample holder in a first direction.

The mixing means further includes means for agitating the contents of the sample holder by moving the platform back and forth rapidly with sudden stops.

In accordance with another aspect of the present invention, a thermogravimetric analyzer is provided including a furnace, a sample holder situated within the furnace, and means for mixing the material to be analyzed and the flux within the sample holder. The mixing means includes a platform within the furnace upon which the sample holder is supported. A tilt member is provided having a first station with a center point and including an upstanding pin, the pin of the first station being offset from the center point of the first station in one direction. The tilt member has a second station with a center point and including an upstanding pin, the pin of the second station being offset from the center point of the second station in another direction. Means are provided for moving the platform relative to the tilt member such that the sample holder aligns with each of the first and second stations, in sequence, and when aligned with each section, moves the platform relative to the tilt member such that the pin of each station abuts and tilts the sample holder in a direction determined by the position of the pin of the aligned station.

The mixing means further includes means for agitating the contents of the sample holder by moving the platform back and forth rapidly with sudden stops.

In accordance with another aspect of the present invention, a thermogravimetric analyzer is provided including a furnace, a sample holder situated within the furnace, and means for mixing the material to be analyzed and the flux within the sample holder. The mixing means includes a platform within the furnace upon which the sample holder is supported. A tilt member is provided having multiple stations. Each station has a center point and includes an upstanding pin. The pin of each section is offset from the center point in a different direction. Means are provided for moving the platform relative to the tilt member such that the sample holder aligns with each of the stations, in sequence, and when aligned with each of the stations, moves the platform relative to the tilt member such that the pin of each of the stations abuts and tilts the sample holder in a direction determined by the position of the pin of the aligned station.

The mixing means further includes means for agitating the contents of the sample holder by moving the platform back and forth rapidly with sudden stops.

In accordance with another aspect of the present invention, a method is provided for preparing a sample for X-ray spectrometry analysis in a thermogravimetric analyzer of the type including a furnace, a movable platform within the furnace, and a tilt member having a plurality of stations, each station having a center point and an upstanding pin mounted at a location offset from the center point of the station in a different direction. The method includes the steps of:

(a) providing a sample holder suitable for use in X-ray spectrometric analysis containing the material to be analyzed and flux;

(b) placing the sample holder onto the platform within the furnace to heat the material to be analyzed and flux;

(c) mixing the material to be analyzed and the flux in the sample holder within said furnace to form a substantially homogeneous mixture by moving the platform relative to the tilt member such that the sample holder aligns with successive stations of the tilt member, and the pin of each aligned station abuts and tilts the sample holder in a direction determined by the location of said pin of the aligned station;

(d) removing the sample holder from the furnace; and (e) allowing the contents of the sample holder to cool and form an X-ray flux bead.

The step of mixing the material to be analyzed and the flux includes repeatedly causing the sample holder to tilt in different directions as the platform is moved.

The step of mixing the material to be analyzed and the flux in the sample holder includes the step of agitating the contents of the sample holder by moving the platform back and forth rapidly with sudden stops.

The platform is rotatable and linearly movable relative to the tilt member to repeatedly tilt the sample holder in different directions.

The thermogravimetric analyzer is associated with an external balance and an internal balance. The method further includes the steps of:

(f) weighing the sample holder with the material to be analyzed and the flux on the external balance prior to placing it into the furnace;

(g) weighing the sample holder with the material to be analyzed and flux within the furnace, after the sample holder is heated;

(h) comparing the weight of the sample holder prior to placing it in the furnace with the weight of the sample holder after it is heated in the furnace to determine the loss on ignition/gain on ignition value of the material to be analyzed; and (i) using the loss on ignition/gain on ignition value of the sample in the X-ray spectrometry analysis.

The step of using the loss on ignition/gain on ignition value includes the steps of:

(j) providing the value to the X-ray spectrometry analysis equipment; and (k) using the value to adjust the results of the X-ray spectrometry analysis.

In accordance with another aspect of the present invention, a sample holder is provided for use in X-ray spectrometry analysis. The sample holder includes a bottom surface having a substantially flat portion. A generally cylindrical side wall is provided having an inclined lower section and an upper section substantially perpendicular to the substantially flat bottom surface portion. An outwardly directed flange is situated on the upper wall portion. An upstanding anti-spill ring extends above the flange.

The sample holder is made of platinum or a material containing platinum.

BRIEF DESCRIPTION OF THE SEVERAL VIEWS OF DRAWINGS

To these and to such other objects that may hereinafter appears, the present invention relates to a method and apparatus for preparing samples for X-ray spectrometric analysis in a thermogravimetric analyzer of the type capable of loss on ignition/gain on ignition analysis as described in detail in the following specification and recited in the annexed claims, taken together with the accompanying drawings, in which like numerals refer to like parts and in which:

FIG. 8 is a perspective view of the sample holder of the present invention; and

FIG. 9 is a top elevation view of the sample holder of the present invention.

DETAILED DESCRIPTION OF THE INVENTION

Figure 1:
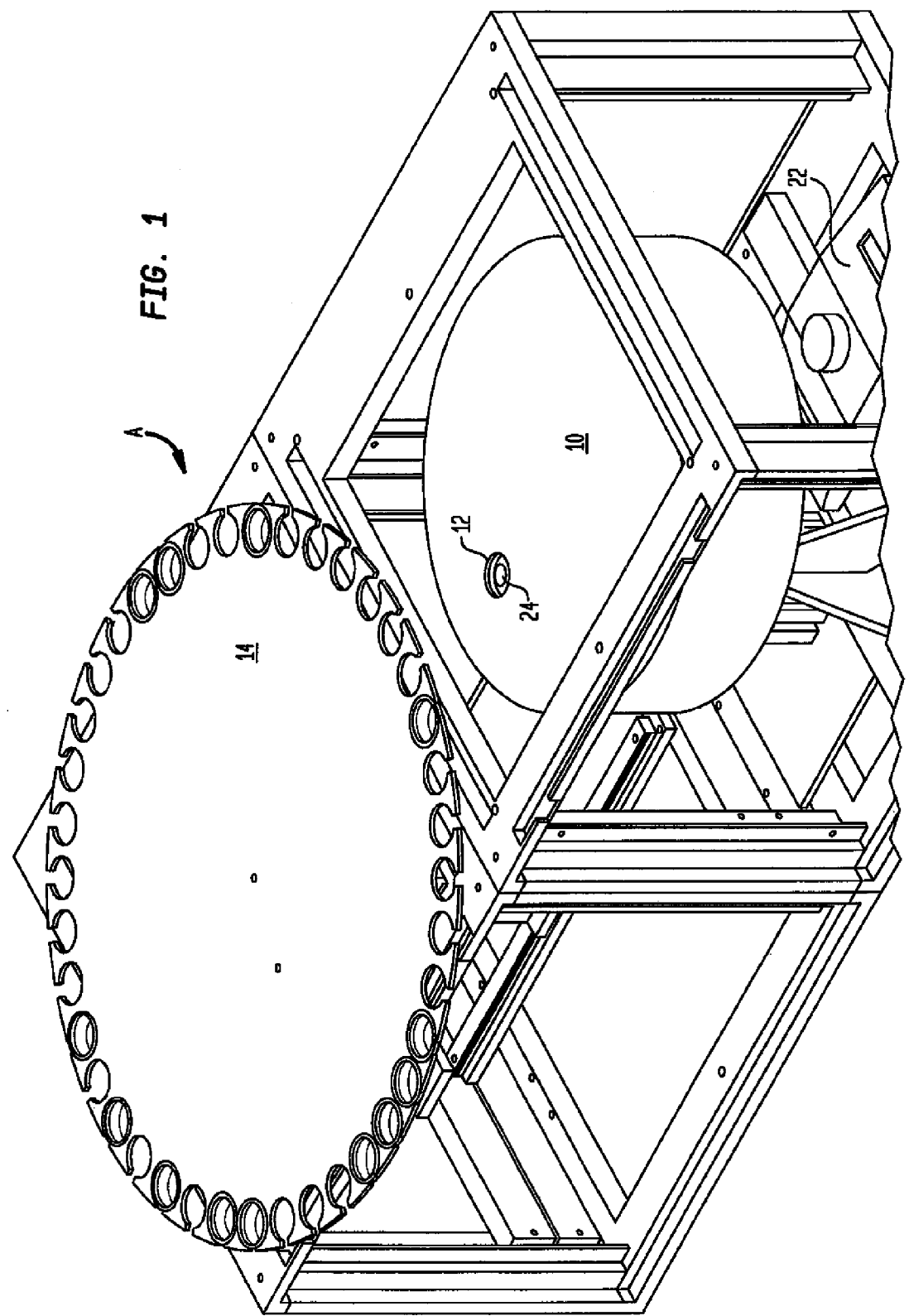
FIG. 1 is a perspective view of the external carousel and furnace of the thermogravimetric analyzer of the present invention.

The present invention uses a thermogravimetric analyzer, generally designated A, which includes a furnace chamber 10 with a door (not shown) which remains closed through all stages of the analysis such that no heat loss occurs and the furnace remains at a uniform temperature throughout the process. Sample holders are placed into and removed from the closed furnace chamber 10 through an opening 12 in the top of the furnace chamber.

FIGS. 8 and 9 illustrate the shape of the sample holder which is employed as part of the present invention to permit the thermogravimetric analyzer perform both the loss on ignition/gain on ignition analysis, and the X-ray sample preparation, in a single, continuous, fully automated process.

As shown in those figures, the sample holder, generally designated H, has a flat bottom surface 11. Extending upwardly from bottom surface 11 is a generally cylindrical wall including an outwardly inclined lower portion 13. The inclination of the wall of lower portion 13 is such that the liquefied sample will always flow from toward the bottom of the sample holder.

Situated above inclined wall portion 13 is a perpendicular (as compared to bottom surface 11) wall portion 15 with an outwardly extending circumferential flange 19. Flange 19 is adapted to rest on the surface of a carousel which carries the sample holders in the present invention and in particular, that portion of the surface proximate the aperture into which the body of the sample holder is received, in order to support the sample holder. Over flange 19 extends an upstanding anti-spill ring 21 designed to prevent the liquefied contents of the sample holder to escape from the sample holder when the sample holder is inclined.

Sample holder H is made of metal, preferably platinum, or a mixture of platinum and gold with a bottom shape to allow the sample to be released from the holder as the sample cools and solidifies.

To prepare the samples, each sample holder H in turn is weighed on a balance or scale (not shown) located outside the furnace to obtain its tare weight. The material to be analyzed is then placed in the sample holder and the sample holder with the material to be analyzed is weighed. Next, flux is placed in the sample holder, the sample holder with the material to be analyzed and the flux is weighed again and the amount of flux adjusted until the proper ratio of material to be analyzed to the flux is obtained. The external balance is connected to a recording system or computer (also not shown) which records the tare weight of each sample holder, the weight of the material to be analyzed, and the weight of the flux, for each sample holder. The material weight and flux weight have to be exact to maintain a fixed ratio.

Alternatively, an auto flux dosing system can be used to perform all of these weighing operations.

The weighed sample holders are then transported, one at a time, to a movable platform situated within furnace chamber 10. The furnace has been pre-heated to the desired temperature to melt the contents of the sample holder to form an X-ray bead. Transport of the sample holders into the furnace is done by placing each of the weighed sample holders in a different one of the openings situated around the periphery of an external carousel 14.

The carousel 14 and a movable ejector, together form an auto-loader mechanism. The ejector includes a vertically movable rod 26 and a pedestal 24. The auto-loader automatically places each sample holder in turn into furnace chamber 10 through opening 12 in the top surface of the furnace chamber. The external carousel is rotated and moved linearly to place each sample holder in alignment with opening 12 in the top of furnace chamber 10.

Figure 2:
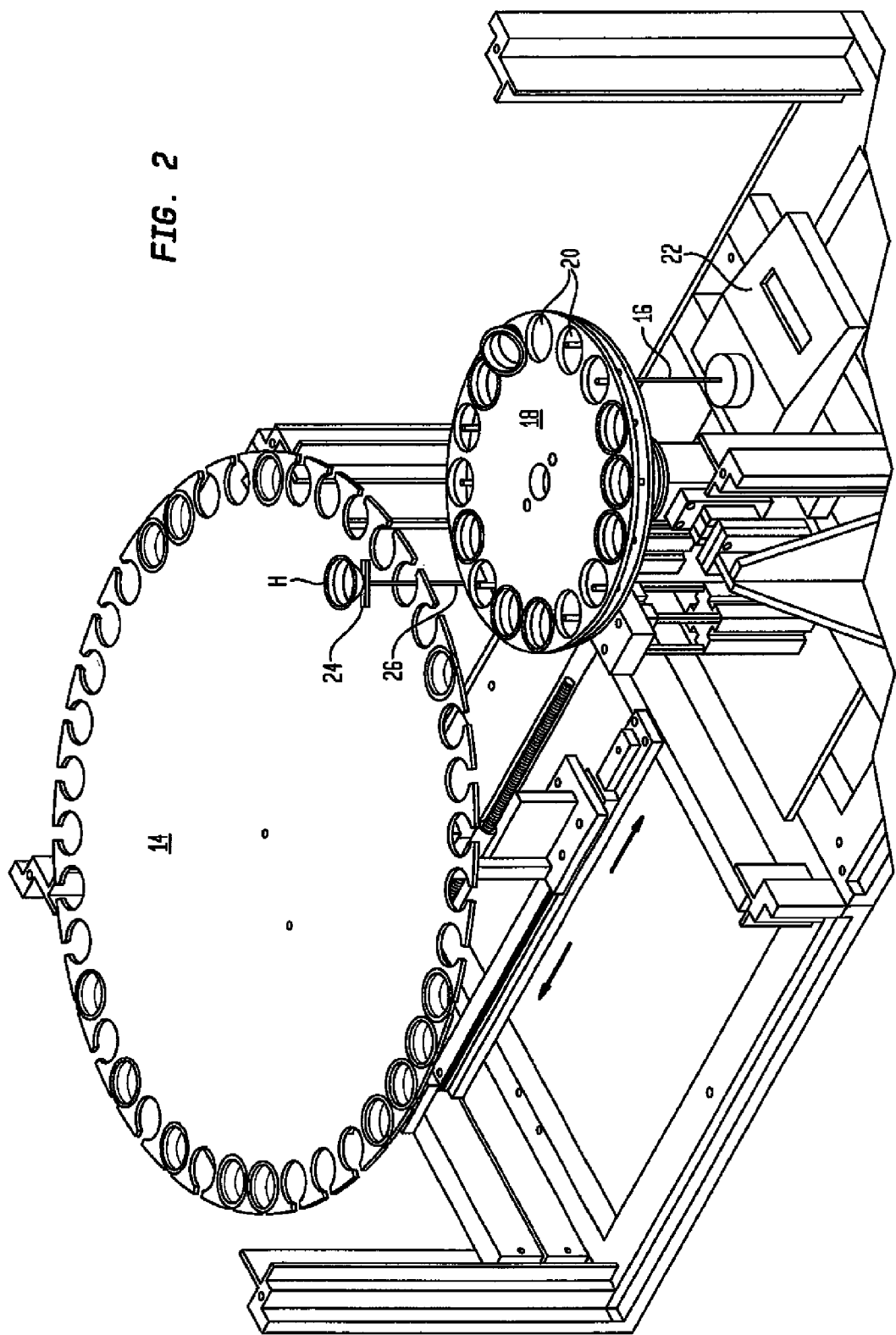
FIG. 2 is a perspective view of the external carousel and furnace of the thermogravimetric analyzer of the present invention, with the housing of the furnace removed.

As best seen in FIG. 2, once the sample holder is properly positioned relative to opening 12, the ejector rod 26 and a pedestal 24 are caused to raise and pick up the sample holder from the carousel opening. The sample holder is held above the plane of carousel 14 while the carousel retracts though the operation of a linear accelerator or similar screw drive located beneath the carousel. The ejector pedestal then moves down, through opening 12, placing the sample holder within the furnace. In particular, the sample holder is placed on a movable platform in the form of a rotatable carousel 18 situated in the furnace.

Internal carousel 18 manipulates the loaded sample holders within the furnace chamber in order to mix the material to be analyzed and the flux in each sample holder and to weigh the contents of the sample holders. Carousel 18 can rotate and can move up and down along its central axis.

The carousel has a series of spaced apertures 20 around its periphery. Apertures 20 are adapted to retain sample holders H and to suspend the sample holders within the furnace chamber. The opening 12 in the top surface of the furnace chamber is positioned such that when carousel 18 comes into position for loading or unloading, one of the apertures 20 in the internal carousel is aligned with opening 12 in the top surface of furnace chamber 10.

The furnace is pre-heated to the desired temperature before the sample holders are loaded into it. While within the furnace chamber, situated on internal carousel 18, the sample holders are heated.

At appropriate points in the testing cycle, carousel 18 is rotationally indexed by a motor 21 such that the sample holders are each in turn aligned with and automatically deposited on a pedestal 17 attached on the end of an upstanding rod 16 associated with an internal balance 22 through vertical motion of the internal carousel. A pneumatic cylinder 28 acts to raise and lower internal carousel 18 to enable the sample holders to be deposited on and removed from pedestal 17 of weighing platform of internal balance 22. The weight of each sample holder is recorded and compared a number of times during the test cycle to perform the loss on ignition/gain on ignition analysis.

Each time internal carousel 18 is raised and lowered by cylinder 28, the sample holders present on the internal carousel are automatically tilted in various directions to mix the material to be analyzed and the flux therein. The repeated mixing of the contents of the sample holders by tilting the sample holders in different directions as the carousel is rotated results in a homogeneous mixture.

Figure 3:
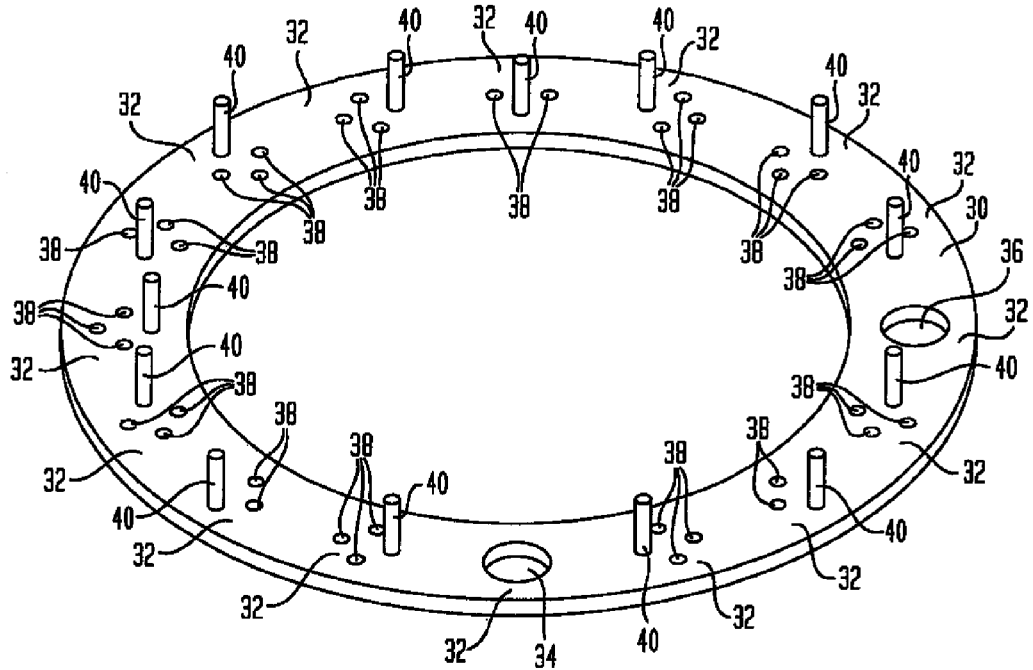
FIG. 3 is a perspective view of the tilting member of the present invention.

The tilting action is caused by the interaction between internal carousel 18 and a stationary, ring-shaped tilt member 30, best seen in FIG. 3. Tilt member 30 rests on the floor of the furnace chamber and has 16 spaced locations, including 14 tilt stations 32 and two openings 34, 36, situated around its body. Each of the stations 32, and openings 34 and 36, aligns with a different one of the 16 apertures 20 in internal carousel 18.

Each tilt station 32 on tilt member 30 has four recesses 38 spaced in a pattern around a center point. The center point of each station aligns with the center of the aperture 20 of internal carousel 18 positioned above that tilt member station. Each station 32 of the tilt member has a single upstanding pin 40 mounted in one of the recesses 38. The pins 40 are placed in different ones of the recesses 38, as one progresses around the tilt member, as illustrated in FIG. 3.

Figure 4:
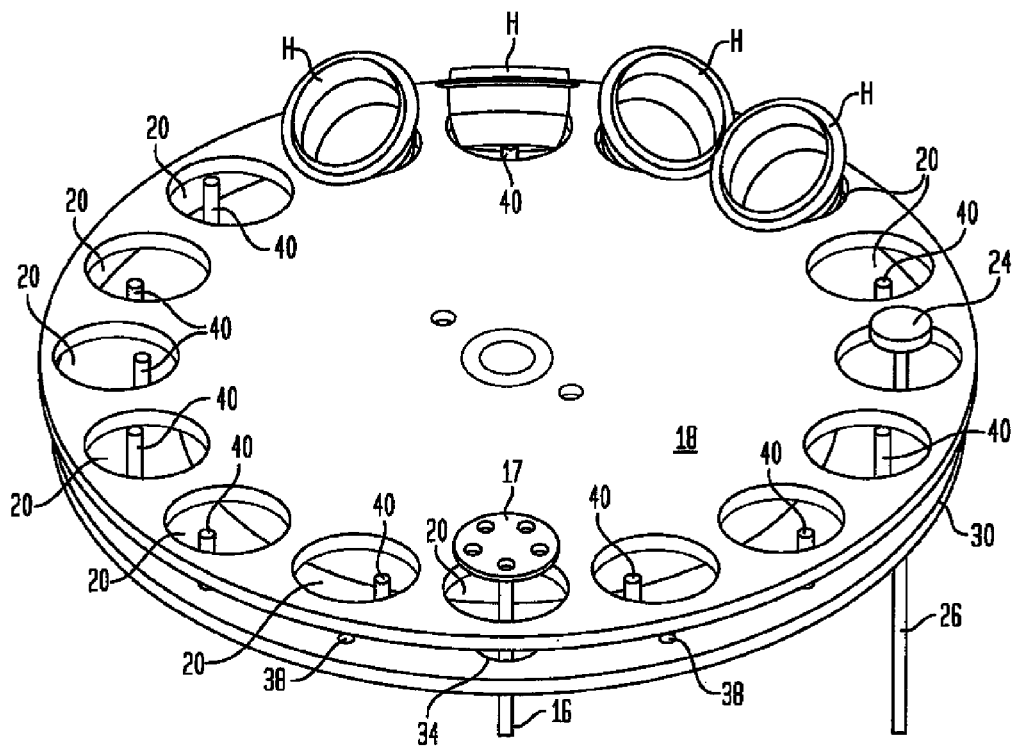
FIG. 4 is a perspective view of the internal carousel and titling member, showing several sample holders being simultaneously tilted.
Figure 5:
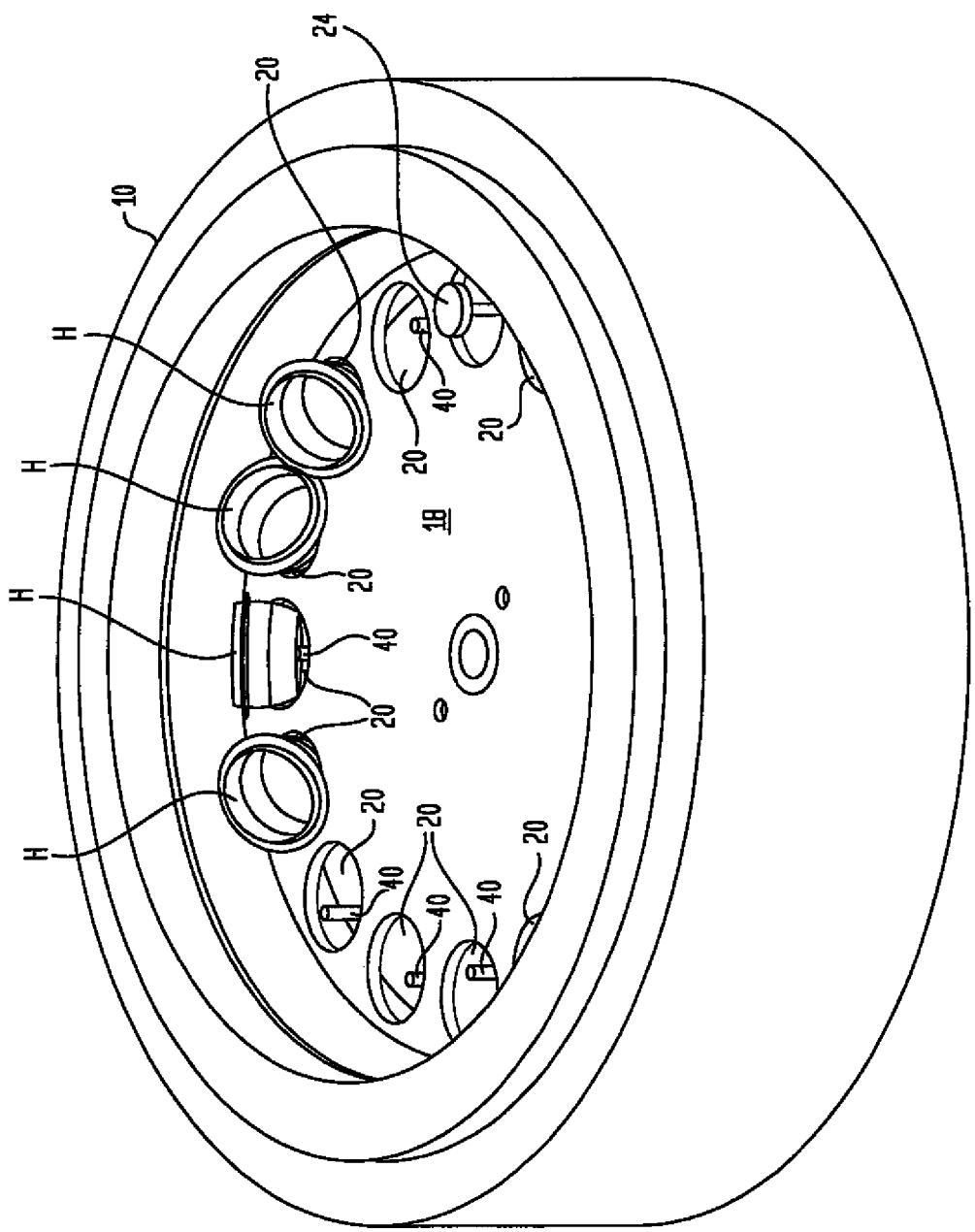
FIG. 5 is a perspective view of the furnace of the thermogravimetric analyzer of the present invention with the top of the furnace removed.
Figure 6:
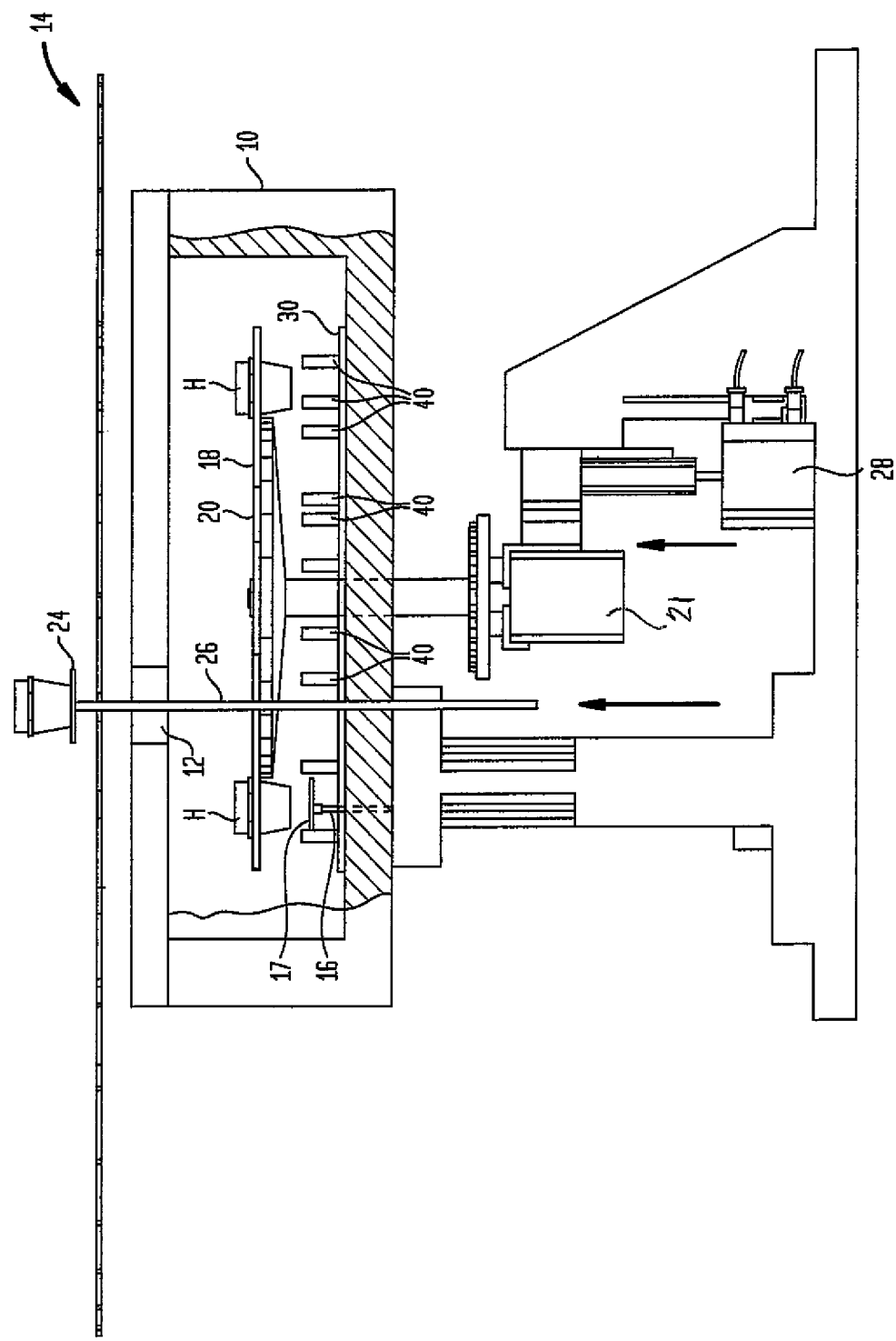
FIG. 6 is a side cross-sectional view of the inside of the furnace of the thermogravimetric analyzer of the present invention showing the internal carousel in its upper position.
Figure 7:
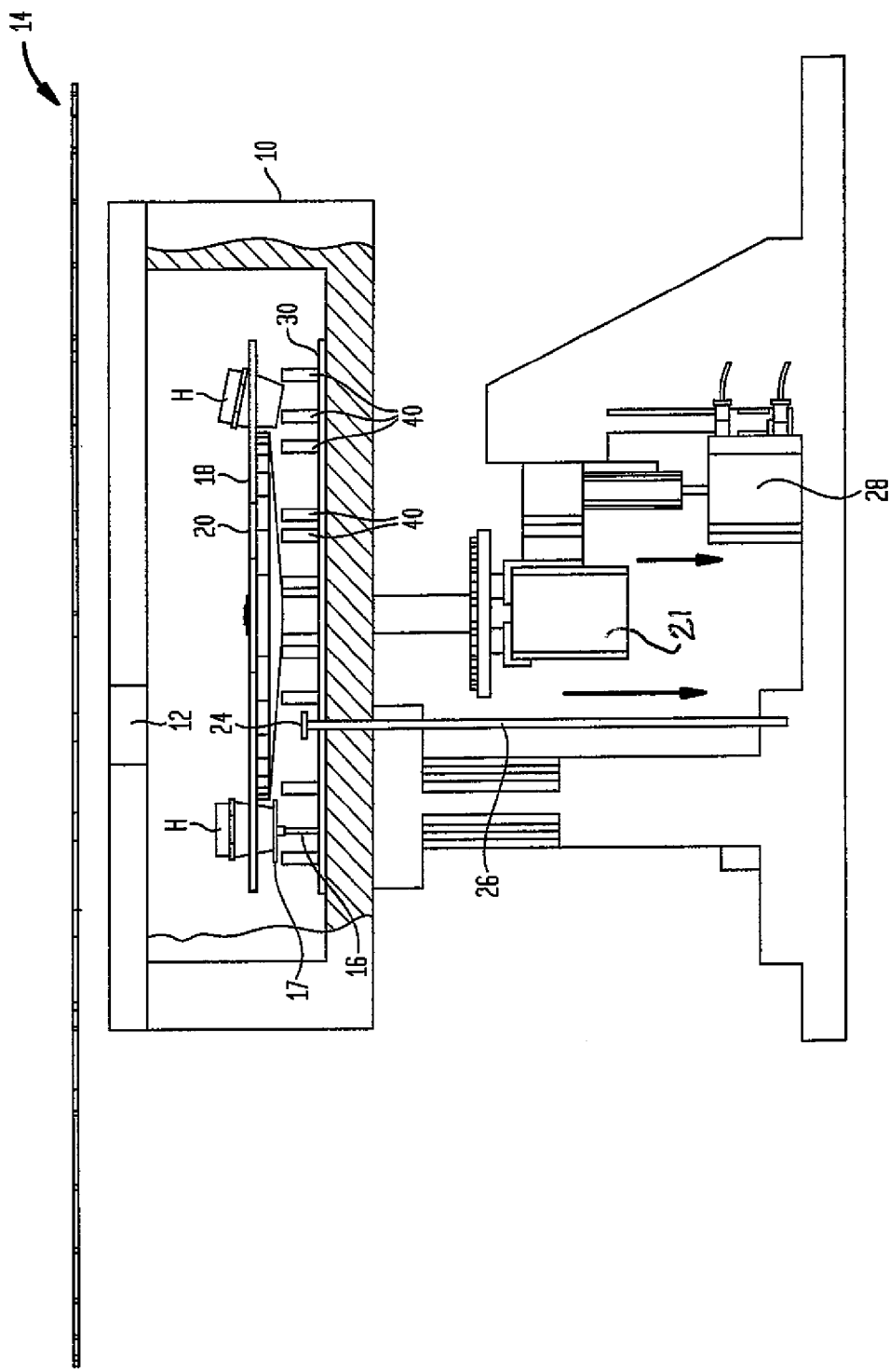
FIG. 7 is a side cross-sectional view of the inside of the furnace of the thermogravimetric analyzer of the present invention showing the internal carousel in its lower position.

As the internal carousel is moved downwardly over the tilt member, as shown in FIGS. 4 and 7, the sample holders in apertures 20 of internal carousel 18 will tilt in one of four different directions, depending upon the position of the pin in the aligned station on the tilt member. The internal carousel is indexed repeatedly by being rotated by motor 21 a distance equal to the distance between the spaced locations of the tilt member after each lowering and raising of the internal carousel. Thus, each aperture 20 of internal carousel is in turn aligned with each tilt station on the tilt member and each time the internal carousel is indexed, the sample holder in each aperture 20 will be tilted in a different one of the four directions. By indexing the internal carousel relative to the tilt member after each up and down movement of the internal carousel, the sample holders will be repeatedly tilted in different directions, causing the material to be analyzed and the flux in each sample holder to mix thoroughly, forming the homogeneous mixture necessary to form the fluxer bead for X-ray analysis.

In some instances, it may be advisable to also agitate the contents of the sample holders to achieve the homogeneous mixture. This can be accomplished by programming motor 21 to rapidly rotate carousel 18 back and forth with sudden stops. Preferably, the agitation of the contents of the sample holders by rapidly rotating the carousel back and forth with sudden stops takes place after at least part of the tilting operation. Thus, agitation of the contents of the sample holders by rapidly rotating the carousel back and forth with sudden stops takes place after the carousel has been indexed, and the sample holders have been tilted four or five times, such that each sample holder has been tilted in each direction at least once before being agitated. When necessary, the tilting and agitating operations can be performed repeatedly until the desired result is obtained.

After each weighing operation, the weighed sample holder is placed back on internal carousel 18. Carousel 18 is indexed and the next sample holder in turn is weighed. The internal balance 22 is connected to a recording system or computer (also not shown) which records data reflecting the difference between the weight of the sample holder as determined by the external balance prior to transporting the sample holder into the furnace and the weight of the sample holder as determined by the internal balance after the last weighing of that sample holder.

It should be noted that aside from 14 tilt stations 32 on tilt member 30, each having an upstanding pin 40, tilt member 32 also has two openings 34 and 36. Opening 36 is aligned with the path of pedestal 24 of the auto-loader. Opening 34 is aligned with pedestal 17 of the weighing platform of internal balance 22. Openings 36 and 34 permit the loading and unloading operations, and the internal weighing operations, to take place without interference from the internal carousel.

Once the final weighing in the test cycle is performed for a particular sample holder, the sample holder is removed through opening 12 on the upper surface of furnace chamber 10 by the same auto-loader mechanism that was used to introduce it, external carousel 14 and ejector pedestal 26. The sample holders are allowed to cool, after which the samples are removed from the holder and placed into the X-ray spectrometer. The X-ray spectrometer has a computer associated with it. The recorded data obtained from the external and internal balances of the thermogravimetric analyzer is provided to the X-ray spectrometer computer.

It will now be appreciated that in the system of the present invention, after the weight of each sample holder, the weight of the material to be analyzed and the weight of the flux have been obtained, the sample holder is placed in the external auto-loader. The sample holders are then transported into the furnace chamber one at a time. The analysis cycle starts the moment the sample holders are introduced into the furnace chamber and continues without manual intervention or disruption due to other sample holders and samples. When the cycle for a particular sample holder or batch is complete, the sample holders and sample are automatically removed from the furnace.

The system of the present invention provides numerous advantages over the prior art. It provides the ability to automatically analyze multiple types of samples for loss on ignition/gain on ignition analysis and/or to simultaneously prepare the beads for X-ray analysis. The apparatus operates safely, with no danger of an operator being burned due to manual handling of sample holders in manual systems, and no need to pour the melted flux to a casting dish. Moreover, the use of single sample holder for the entire process provides huge savings by reducing the need of crucible cleaning, required in the conventional dual crucible casting dish operation. The present invention also provides the convenience of unattended operation, savings in electricity or gas; and better reproducibility of the analytical results.

While only a single preferred embodiment of the present invention has been disclosed for purposes of illustration, it is obvious that many modifications and variations could be made thereto. It is intended to cover all of those modifications and variations which fall within the scope of the present invention, as defined by the following claims.

I claim:

1. A thermogravimetric analyzer for analyzing a sample material and flux comprising a furnace, a sample holder situated with said furnace, means for mixing the sample material to be analyzed and the flux within said sample holder, said mixing means comprising a platform within said furnace upon which said sample holder is supported, a tilt member having a station with a center point and an upstanding pin offset from said center point, and means for moving said platform relative to said tilt member such that said sample holder aligns with said station and said pin abuts and tilts said sample holder in a first direction.

2. The analyzer of claim 1 wherein said mixing means further comprises means for agitating the sample material and flux in the sample holder by rapidly moving said platform back and forth with sudden stops.

3. A thermogravimetric analyzer for analyzing a sample material and flux comprising a furnace, a sample holder situated with said furnace, means for mixing the sample material to be analyzed and the flux within said sample holder, said mixing means comprising a platform within said furnace upon which said sample holder is supported, a tilt member having a station with a center point and an upstanding pin offset from said center point, and means for moving said platform relative to said tilt member such that said sample holder aligns with said station and said pin abuts and tilts said sample holder and thereafter rapidly moving said platform back and forth with sudden stops.

4. A thermogravimetric analyzer for analyzing a sample material and flux comprising a furnace, a sample holder situated with said furnace, means for mixing the sample material to be analyzed and the flux within said sample holder, said mixing means comprising a platform within said furnace upon which said sample holder is supported, a tilt member having a station with a center point and an upstanding pin offset from said center point, and means for moving said platform relative to said tilt member such that said sample holder aligns with said station and said pin abuts and tilts said sample holder in one direction, said tilt member having a second station with a center point and comprising an upstanding pin, said pin of said second station being offset from said center point of said second station in another direction, and means for moving said platform relative to said tilt member such that said pin of each station abuts and tilts said sample holder in a direction determined by the position of said pin of said aligned station.

5. The analyzer of claim 4 wherein said mixing means further comprises means for agitation the sample material and flux in the sample holder by rapidly moving said platform back and forth with sudden stops.

6. A thermogravimetric analyzer for analyzing a sample material and flux comprising a furnace, a sample holder situated with said furnace, means for mixing the sample material to be analyzed and the flux within said sample holder, said mixing means comprising a platform within said furnace upon which said sample holder is supported, a tilt member having a station with a center point and an upstanding pin offset from said center point, and means for moving said platform relative to said tilt member such that said sample holder aligns with said station and said pin abuts and tilts said sample holder in a first direction in each station, and means for moving said platform relative to said tilt member such that said sample holder aligns with each of said stations, in sequence, and when aligned with each of said stations, moves said platform relative to said tilt member such that said pin of each of said stations abuts and tilts said sample holder in a direction determined by the position of said pin of said aligned station.

7. The analyzer of claim 6 wherein said mixing means further comprises means for agitation sample material and flux in the sample holder by rapidly moving said platform back and forth with sudden changes.

\* \* \* \* \*